US006252195B1

(12) United States Patent
Mosavi et al.

(10) Patent No.: US 6,252,195 B1
(45) Date of Patent: *Jun. 26, 2001

(54) METHOD OF FORMING BLIND HOLES IN SURGICAL NEEDLES USING A DIODE PUMPED ND-YAG LASER

(75) Inventors: Reza K. Mosavi, Alto, GA (US); Timothy L. Irwin, Rochester, NY (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/298,876

(22) Filed: Apr. 26, 1999

(51) Int. Cl.[7] .................................................. B23K 26/00
(52) U.S. Cl. ................................. 219/121.69; 219/121.85
(58) Field of Search ........................... 219/121.7, 121.71, 219/121.69, 121.85

(56) References Cited

U.S. PATENT DOCUMENTS

| 4,808,789 | * | 2/1989 | Muncheryan ..................... 219/121.6 |
| 4,910,377 | * | 3/1990 | Matsutani et al. .......... 219/121.68 X |
| 5,012,066 | * | 4/1991 | Matsutani et al. .......... 319/121.69 X |
| 5,059,764 | * | 10/1991 | Baer ............................ 219/121.69 X |
| 5,889,255 | * | 3/1999 | Bogart et al. .................... 219/121.65 |

FOREIGN PATENT DOCUMENTS 63-140789 * 6/1988 (JP) ................................ 219/121.71

* cited by examiner

Primary Examiner—Samuel M. Heinrich
(74) Attorney, Agent, or Firm—Emil Richard Skula

(57) ABSTRACT

A method of laser drilling surgical needles. The method utilizes a diode pulsed laser to produce a laser beam consisting of a train of high energy pulses.

8 Claims, 5 Drawing Sheets

Penta-Pulse Temporal Profile

Energy (Joules)

Timebase: 50 μs/div

Time ( microseconds)

Pulse Width= 50 μs    Pulse Energy= 50 μJ

Dual Pulse Temporal Profile

Energy (Joules)

Timebase: 20 μs/div

Time ( microseconds)

Pulse Width= 50 μs    Pulse Energy= 50 μJ

FIG. 1 *Prior Art*

FIG. 2
_Prior Art_
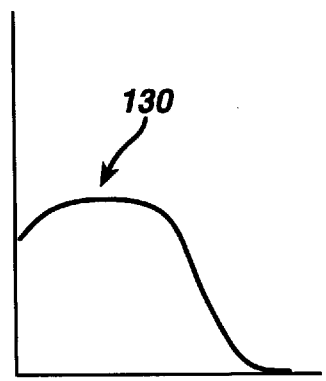

Penta-Pulse Temporal Profile

Time ( microseconds)

Pulse Width= 50 μs    Pulse Energy= 50 μJ

Dual Pulse Temporal Profile

Time ( microseconds)

Pulse Width= 50 μs    Pulse Energy= 50 μJ

METHOD OF FORMING BLIND HOLES IN SURGICAL NEEDLES USING A DIODE PUMPED ND-YAG LASER

TECHNICAL FIELD

The field of art to which this invention relates is surgical needles, in particular, a method of drilling blind holes in surgical needles using lasers.

BACKGROUND OF THE INVENTION

Surgical needles and attached sutures are well known in the art. Surgical needles typically have a distal pointed end and a proximal suture mounting end. The suture mounting end can have several structural configurations for receiving a suture tip, including channels and blind holes. The distal end of a suture is typically mounted to the proximal end of a surgical needle in several ways. For example the distal end or tip of the suture may be inserted into a channel, and the channel is then mechanically swaged to lock the suture in the channel. Or, the distal end or tip of a suture may be mounted into a bore hole drilled into the proximal end of a needle. The proximal end of the needle is then mechanically swaged such that the suture end is mechanically locked into the bore hole. Alternatively, sutures may be mounted to surgical needles using adhesives, epoxies, shrink tubing and other known mounting techniques.

The use of blind bore holes to mount sutures to surgical needles has become the mounting method of choice for many types of surgical needles. The needles having suture mounted in this manner may have less resistance to penetration when moved through tissue. Blind bore holes are typically drilled into the proximal ends of needles using one of two conventional methods. One method of drilling surgical needles is to use mechanical drills. The other method of drilling blind bore holes is to use lasers. Mechanical drilling is known to have several disadvantages including mechanical alignment, tool wear, constant adjustments, the inability to drill small diameter holes, and relative slowness of the mechanical drilling process. The use of laser drilling overcomes many of these problems. The laser uses a beam of light energy to form the blind bore hole by liquefying the metal and causing it to be expelled from the proximal end of the needle. Accordingly, in laser drilling there is no mechanical contact with needle by the drilling apparatus, tool wear is not a problem, alignment problems and adjustments are minimized, and drilling is considerably more time effective, allowing for high production throughput.

Although the use of conventional laser systems to drill surgical needles has many advantages, there are also some problems which are attendant with their use. Laser drilling equipment is typically more sophisticated and complex than mechanical drilling equipment and requires highly skilled operators. In addition, the laser drilling may produce a bore hole which does not have an entirely smooth interior surface because of residual slag resulting from the expulsion of the molten metal. The slag may interfere with the insertion of a suture into a bore hole.

It is known that to produce a smooth bore hole it is desirable to remove metal from a bore hole through evaporation and plasma formation rather than a melting process. This can be done by using pulsed Nd-YAG lasers. Such lasers produce a train of short pulses having sufficient energy to remove small amounts of material with each pulse, thereby producing a high quality bore hole. The duration of the pulses is typically in the 10 microseconds to 100 microseconds range.

Presently, short pulses for drilling surgical needles are produced using a conventional flash lamp pumped Nd-YAG laser as an oscillator to produce an optical pulse range from 200 microseconds to 600 microseconds duration. This optical pulse is then intensity modulated by an electro-optical modulator or similar device into a plurality of short pulses (i.e., a pulse train). The duration of these short pulses and their frequencies are controlled by the modulator parameters. The pulse train then enters a conventional flash lamp pumped Nd-YAG amplifier and is amplified to produce a high power intensity beam. The high power intensity beam is then focused on the rear or proximal end face of a surgical needle to drill a blind hole into the proximal end of the needle.

Because of the inherent limitations of flash lamp pulsing, the production of short pulses requires modulation of the main pulse by means of an electro-optical modulator, which in turn requires an optical polarizer and analyzer. The addition of these optical devices along the path of the laser beam causes the loss of some optical energy, and is associated with some difficulty in keeping the optical devices optically aligned in the manufacturing environment. The electro-optical modulator (Pockles Cell) requires the use of high voltage electronics which in turn require high maintenance and extensive safety precautions. The flash lamp pumped laser oscillator and amplifier use both high voltage power supplies and capacitor banks to store energy for discharging into the flash lamp. The flash lamp is believed to be an inefficient way of pumping a laser rod, since most of the energy is dissipated in the form of heat which must be removed by a cooling system. The power supply, capacitor banks, and cooling system require significant amounts of space, maintenance and troubleshooting. The heat dissipated in the laser rod from flash lamp operation also causes thermal lensing of the rod, which deteriorates the quality of the laser beam. Another problem observed with the existing flash lamp pumped method is usable flash lamp life. The average flash lamp may have a life of about 500 to 600 hours. This requires shutting down the laser drilling system every 600 or so hours to replace the flash lamp thereby interrupting production, and necessitating maintenance and repair.

Accordingly, there is a need in this art for improved pulsed laser systems which overcome the disadvantages of a flash lamp pulsing system.

SUMMARY OF THE INVENTION

Therefore, it is an object of the present invention to provide a method of pulsed laser drilling of surgical needles which is efficient, and which eliminates the need for an optical polarizer, an electro-optical modulator, an analyzer, a flash lamp and associated power supplies and capacitor banks.

It is also an object of the present invention to provide for a pulsed laser drilling system which is easier to cool, which has reduced heating of the laser rod and reduced thermal lensing effect, and which can operate significantly longer than a flash lamp pumped system without having downtime.

Accordingly, a method of laser pulsed drilling of surgical needles is disclosed. The method consists of providing a laser drilling apparatus which utilizes an oscillator consisting of an Nd-YAG crystal rod and a plurality of high power laser diode arrays. An optical pulse is produced by the laser apparatus. The pulse is focused on the proximal end of a surgical needle to make a blind hole.

These and other advantages of the present invention will become more apparent from the following description and accompanying drawings.

BRIEF DESCRIPTION OF THE DRAWINGS

FIG. 2 is a schematic diagram of a typical optical pulse produced by a flash lamp pumped Nd-YAG laser oscillator of the prior art.

DETAILED DESCRIPTION OF THE PREFERRED EMBODIMENTS

Figure 1:
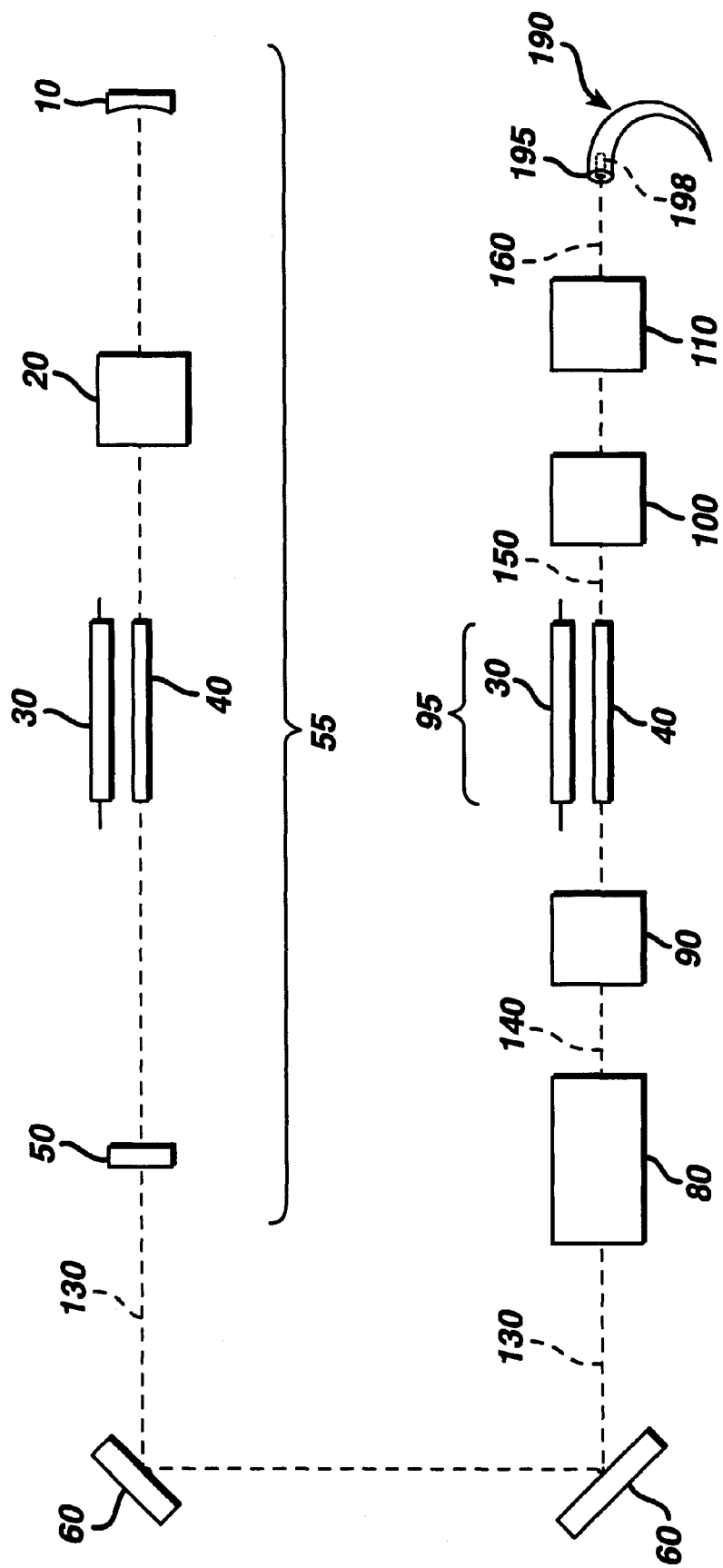
FIG. 1 is a schematic diagram of a flash lamp pulsed laser drilling system of the prior art.
Figure 3:
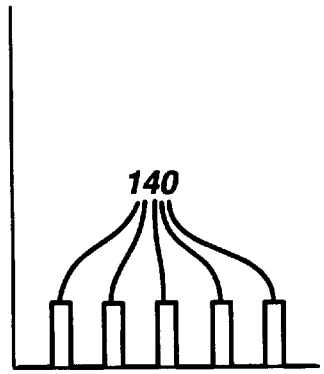
FIG. 3 is a schematic diagram illustrating a typical train of pulses created by modulating the single optical pulse of FIG. 2.
Figure 4:
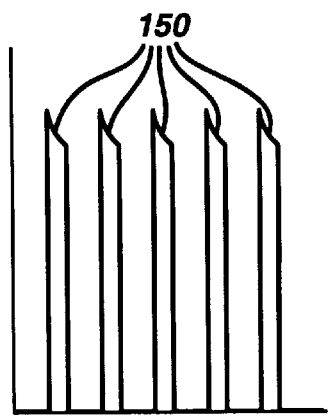
FIG. 4 is a schematic view showing the train of pulses of FIG. 3 after amplification.

A schematic diagram of a flash lamp pumped Nd-YAG laser drilling system of the prior art is illustrated in FIG. 1. As seen in FIG. 1, the system has a rear, convex 100% reflective mirror 10 aligned with a beam polarizer 20, and an Nd-YAG laser rod 40. Adjacent to the Nd-YAG laser rod 40 is a flash lamp 30. Aligned with laser rod 40 is an output coupler mirror 50. The combination of the mirror 10, the beam polarizer 20, the flash lamp 30, the laser rod 40, and the output coupler mirror 50 comprises the laser oscillator 55. The flash lamp 30 pumps the Nd-YAG rod 40 into a higher energy level, and the mirrors 10 and 50 cause the laser oscillation to occur. The beam polarizer 20 linearly polarizes the laser beam. An optical pulse 130, as illustrated in FIG. 2, then exits the output coupler mirror 50 and reflects sequentially off of a pair beam bending flat mirrors 60. The optical pulse 130 is modulated by the electro-optical modulator 80 into a short pulse train 140 as seen in FIG. 3. The pulse train 140 then goes into an analyzer 90, and then enters the amplifier 95. Amplifier 95 consists of flash lamp 30 and Nd-YAG laser rod 40. The short pulse train 140 is then amplified to pulse train 150 as seen in FIG. 4 and goes through the beam expander 100, and then the focusing optics assembly 110 to form beam 160. Beam 160 is then directed at the proximal end face 195 of the surgical needle 190 to form blind hole 198.

Figure 5:
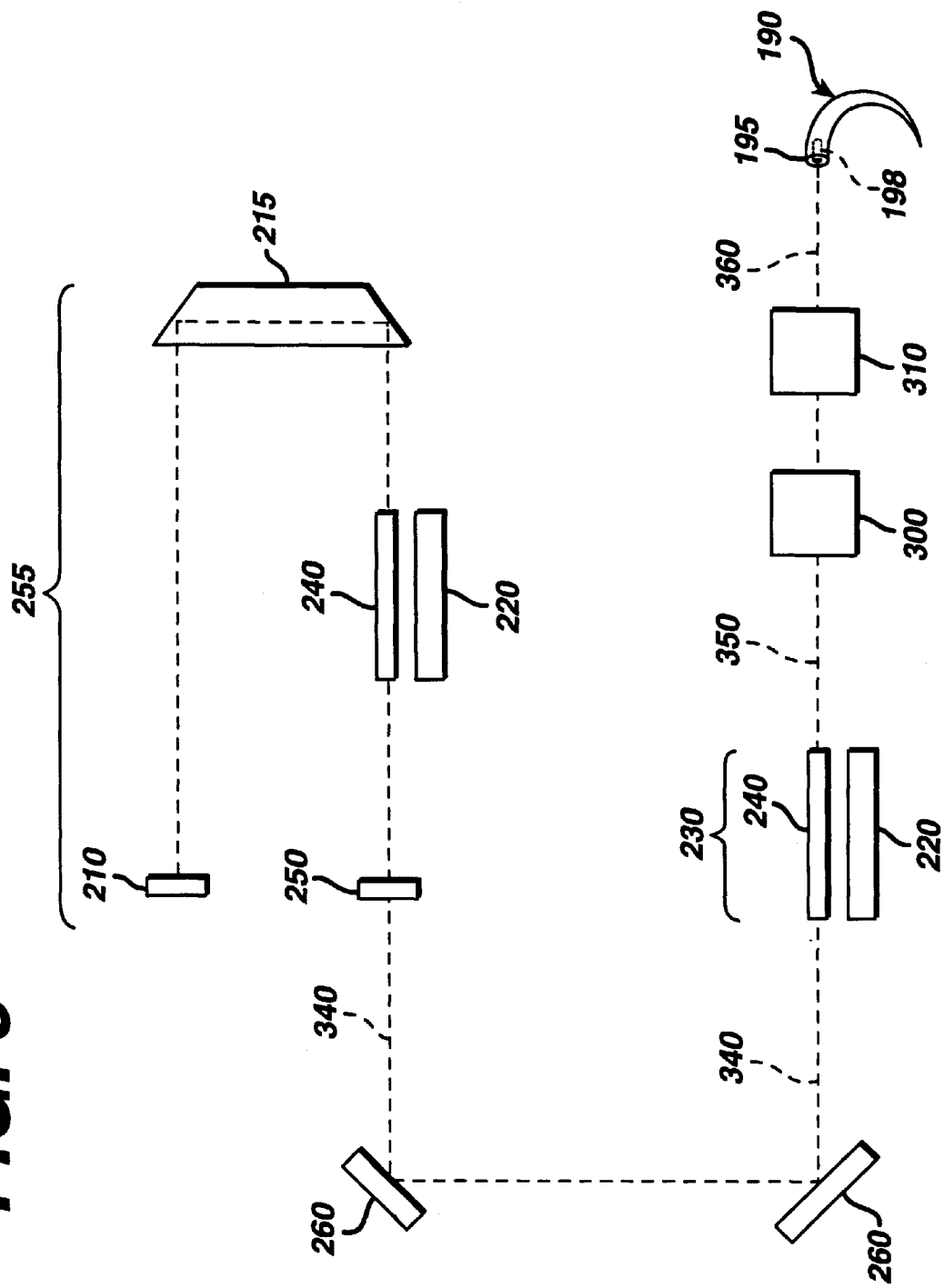
FIG. 5 is a schematic diagram illustrating a laser diode pumped Nd-YAG laser oscillator and amplified system of the present invention useful for drilling surgical needles.
Figure 6:
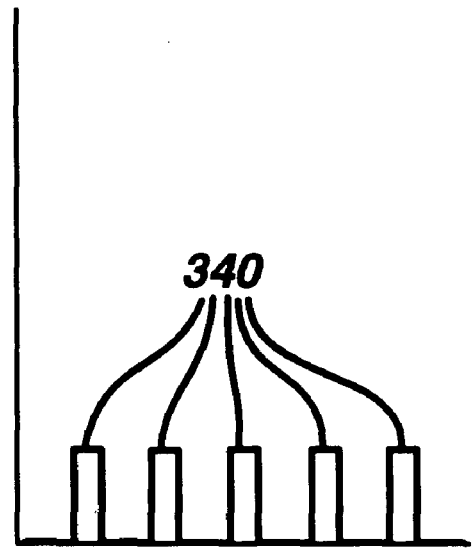
FIG. 6 is a schematic diagram illustrating a train of optical pulses produced by the laser diode pumped Nd-YAG laser oscillator of FIG. 5.
Figure 7:
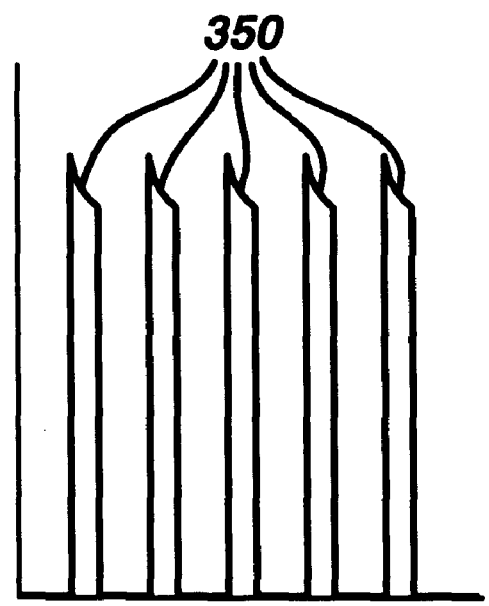
FIG. 7 is a schematic diagram illustrating the train of pulses of FIG. 6 after amplification.
Figure 8A:
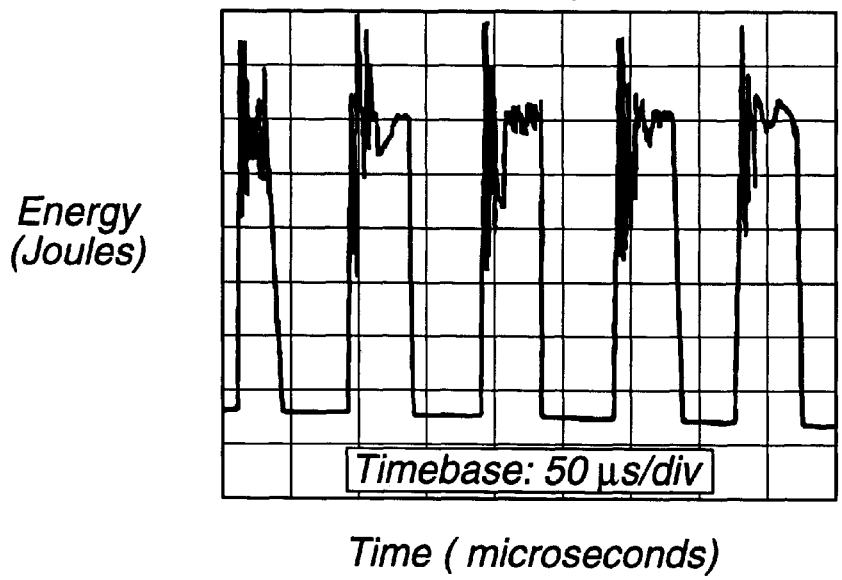
FIGS. 8A & B illustrate on an oscilloscope trace of optical pulses produced by the laser diode pumped Nd-YAG laser oscillator of FIG. 5.
Figure 8B:
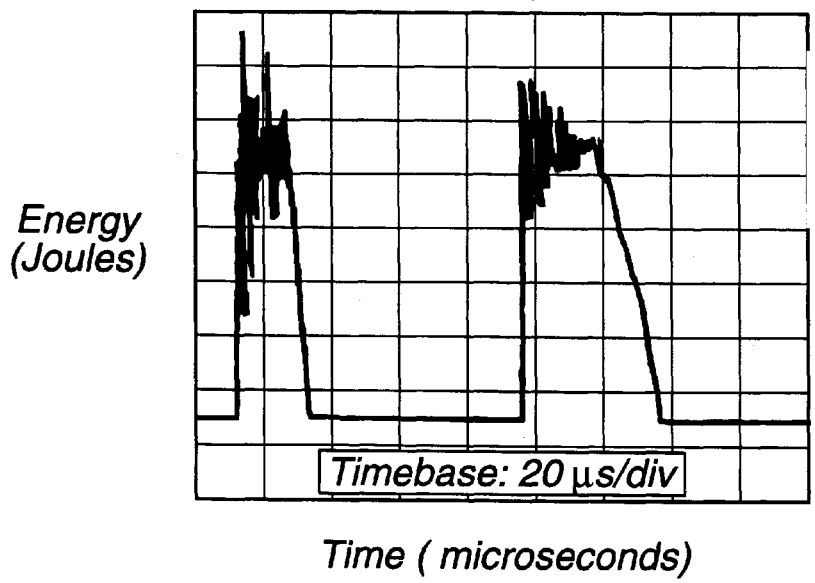

Referring now to FIG. 5, a schematic of a preferred embodiment of a laser diode pumped Nd-YAG laser system of the present invention useful for drilling surgical needles is disclosed. The system consists of a curved, 100% reflective rear mirror 210, a beam bending prism 215, a small diameter Nd-YAG rod 240, a group of high power laser diode arrays 220, and a partially transmitting outer coupler mirror 250. This establishes the laser oscillator 255. A solid state power supply (not shown in FIG. 5) drives the laser diode arrays for different powers, frequencies and pulse widths. The driving frequencies can range up to 10 k Hz. The laser diode arrays 220 are made up of a number of diode bars. The diode arrays 220 emit radiation pulses in the narrow spectral width fitting to the small absorption bands of the Nd-YAG rod. The Nd-YAG rod 240 is optically pumped by the laser diode arrays 220 in the presence of the two mirrors 210 and 250, causing the laser oscillation to occur. The pulse width and pulse frequency of the Nd-YAG rod laser emission follows the pulse width and pulse frequency of the diode arrays. Nd-YAG optical pulses in the range of 5 microseconds to 100 microseconds can be produced. These pulses come in the form of a pulse train 340 as seen in FIG. 6. The pulse train 340 sequentially goes through a pair of beam bending flat mirrors 260 before it is sent to the amplifier section 230. Amplifier section 230 consists of an Nd-YAG rod 240 and a group of high power arrays 220. It should be noted that in both the laser oscillator 255 and laser amplifier 230, the laser diode arrays 220 pump the Nd-YAG rod 240 along the side. The power of the high powered laser diode bar 240 is in the range, preferably, of about 40 to 50 watts, and is sufficintly effective to produce the pulse train desired. Each array 220 can have "N" number of bars and these arrays can be arranged in different configurations around the Nd-YAG rod to illuminate the rod. The amplified pulse train 350 as seen in FIG. 7 is then sent to beam expander 300, and a focusing optics assembly 310 where the laser beam 360 finally is focused on the proximal end face 195 of surgical needle 190. When the amplified high power short pulses 360 are focused on the end face 195 of needle 190, they remove metal in the form of evaporation and plasma formation, which produces high quality blind holes 198.

The diode pumped Nd-YAG laser drilling systems of the present invention have many advantages over the flash lamp pumped systems of the prior art. Using the laser diode pulsed Nd-YAG laser drilling systems of the present invention, it is now possible to eliminate the optical polarizer, electro-optical modulator, analyzer, flash lamp and its associated power supplies and capacitor banks used in a conventional flash lamp pulsed system.

In addition, it is now possible to obtain higher beam quality due to the reduction of thermal lensing effect caused by excessive heat input to the rod by flash lamp. Laser beam alignment and maintenance are simpler and easier due to the elimination of the pulse modulating system of the prior art.

The laser drilling systems of the present invention have higher energy efficiency, and reduced laser downtime since it is no longer necessary to replace flash lamps.

The 100% reflective rear mirrors useful in the laser systems of the present invention include conventional, commercially available curved reflective mirrors such as those available from CVI Laser Optics Corp., Albuquerque, N. Mex., Lambda Research Optics Inc., Cerritos, Calif., and Coherent Auburn Group, Auburn, Calif. The size of the mirrors will preferably be about Ø0.5"×0.25" thick. The reflective mirrors function to create the lasing process.

The Nd-YAG laser rods useful in the laser systems of the present invention include conventional, commercially available small diameter rods such as 1.0% Nd-YAG. The size of the laser rods will be sufficient to effectively convert enough of the 808 nm pump light into 1064 nm lasing light. The size of the rods will typically be from about Ø2.5 mm to about Ø6.0 mm, more typically about Ø2.5 mm×100 mm to about Ø6.0 mm to 200 mm and preferably about Ø3.0 mm×140 mm to about Ø4.0 mm×140 mm. The laser rods function to convert pump light energy into lasing light energy. The laser rods are available from Litton Airtron Synoptcs, Charlotte, N.C. as Part No. Nd:YAG 3×104 mm. The laser diode bars are available from Coherent, Inc. as Part No. ULPS156E/9/3.

The partially transmitting output coupler mirrors useful in the practice of the present invention include conventional, commercially available output coupler mirrors such as ⌀0.5"×0.25" thick dielectrically coated substrates.

The coupler mirrors function to maintain the lasing process inside the resonator while at the same time allowing some of the resonator light to exit.

The laser diode arrays useful in the systems of the present invention include conventional, commercially available diode arrays such as radial arrays. The diode arrays function to generate 808 nm pump light energy. The diode arrays will typically consist of a plurality of laser bars. The laser bars are conventional, commercially available laser bars such as AlGaAs. The laser bars function to convert electrical energy into 808 nm optical energy.

The solid state power supplies useful to power the diode arrays include conventional, commercially available power supplies such as laser diode drive. The power supplies function to convert standard wall plug electrical power into pulsed electrical power. The capacity of the power supplies will be sufficient to effectively provide pulsed electrical power. The power will typically range from about 10 watts to about 500 watts, more typically about 50 watts to about 400 watts, and preferably about 100 watts to about 350 watts.

The beam bending flat mirrors useful in the laser systems of the present invention include conventional commercially available beam bending flat mirrors such as dielectrically coated glass substrates. The beam bending flat mirrors function to reflect laser light energy.

The beam expander useful in the practice of the present invention includes conventional, commercially available beam expanders such as the ones from CVI Laser Optics Corp. or Lambda Research Optics Inc. and Coherent Auburn Group. The beam expander functions to expand the diameter of the laser beam while at the same time collimating the laser beam.

The focusing optics assemblies useful in the practice of the method of the present invention includes conventional, commercially available optics assemblies such as 100 mm or 150 mm focusing lenses. The optics assembly functions to focus the laser light energy into a small spot.

As mentioned previously, the parts used in the laser systems of the present invention are commercially available. For example, the rear mirror can be purchased from JML Direct Optics in Rochester, N.Y. as Part No. MPC14700/505, the prism may be purchased from JML Direct Optics as Part No. PDC 16120/104, while the output coupler mirror, the beam bending mirror, beam expander and focusing lens can be purchased form JML Direct Optics as Part Nos. CMN 11225/202/xxx, MCL 15100/505, 52340/104 and CLL 13745/104 respectively.

The laser beams used to drill surgical needles in the process of the present invention will have power, pulse frequency, and pulse width sufficiently effective to drill blind holes in metal surgical needles. The power of the beam will typically be about 5 watts to about 100 watts, more typically about 10 watts to about 50 watts, and preferably about 25 watts to about 45 watts. The pulse width of the beam will typically be about 5 microseconds to about 1 millisecond, more typically about 7 microseconds to about 200 microseconds, and preferably about 10 microseconds to about 100 microseconds. The frequency of the beam will typically be about single pulse to about 100 kHz, more typically about 1 kHz to about 50 kHz, and preferably about 1.5 kHz to about 10 kHz. The power of the beam is varied by varying the pulse energy and/or pulse frequency. The frequency of the beam is varied by the operator. The pulse width of the beam is varied by the operator.

Although this invention has been shown and described with respect to detailed embodiments thereof, it will be understood by those skilled in the art the various changes in form and detail thereof may be made without departing from the spirit and scope of the claimed invention.

What is claimed is:

1. A method of laser drilling surgical needles, the method comprising the steps of:

providing a diode pulsed laser Nd-YAG drilling system;

producing a laser beam comprising a train of laser pulses having sufficient power to effectively drill a blind hole in a surgical needle;

directing the beam of laser pulses onto a proximal end of a surgical needle to produce a blind bore hole in the surgical needle suitable for receiving an end of a surgical suture.

2. The method of claim 1 wherein the diode pulsed laser drilling system comprises:

a curved rear mirror;

a first Nd-YAG rod;

a plurality of high power laser diode arrays;

a partially transmitting output coupler mirror;

a solid state power supply to drive the diode arrays;

first and second beam bending flat mirrors;

a second Nd-YAG rod;

a second plurality of high power laser diode arrays;

a beam expander; and, a focusing optics assembly.

3. The method of claim 1, wherein the beam has a power of about 5 watts to about 100 watts.

4. The method of claim 1 wherein the beam has a pulse width of about 5 microseconds to about 1 millisecond.

5. The method of claim 1, wherein the frequency of the beam is from about one pulse to about 100 kHz.

6. The method of claim 1, wherein the beam has a power of about 25 watts to about 45 watts.

7. The method of claim 1, wherein the pulse width of the beam is about 10 microseconds to about 100 microseconds.

8. The method of claim 1, wherein the frequency of the beam is about 1.5 KHz to about 10 kHz.

* * * * *